United States Patent
Cao et al.

(10) Patent No.: US 12,403,079 B2
(45) Date of Patent: Sep. 2, 2025

(54) INGREDIENT IN SUNSCREEN COMPOSITIONS

(71) Applicants: MAGIC BLUE, LLC, Bethesda, MD (US); UNIVERSITY OF MARYLAND, College Park, MD (US)

(72) Inventors: Kan Cao, Bethesda, MD (US); Chandamany Arya, Ellicott City, MD (US); Jasmin El Kordi, Vienna, VA (US)

(73) Assignees: Magic Blue, LLC, Bethesda, MD (US); University of Maryland, College Park, MD (US)

( * ) Notice: Subject to any disclaimer, the term of this patent is extended or adjusted under 35 U.S.C. 154(b) by 212 days.

(21) Appl. No.: 17/766,598

(22) PCT Filed: Oct. 16, 2020

(86) PCT No.: PCT/US2020/055958
§ 371 (c)(1),
(2) Date: Apr. 5, 2022

(87) PCT Pub. No.: WO2021/076875
PCT Pub. Date: Apr. 22, 2021

(65) Prior Publication Data
US 2024/0099952 A1    Mar. 28, 2024

Related U.S. Application Data

(60) Provisional application No. 62/973,654, filed on Oct. 18, 2019.

(51) Int. Cl.
  *A61K 8/49*    (2006.01)
  *A61K 8/02*    (2006.01)
  *A61Q 17/04*   (2006.01)

(52) U.S. Cl.
  CPC .......... *A61K 8/4926* (2013.01); *A61K 8/0229* (2013.01); *A61Q 17/04* (2013.01); *A61K 2800/30* (2013.01)

(58) Field of Classification Search
  CPC ................ A61K 8/4926; A61K 8/0229; A61K 2800/30; A61K 8/49; A61Q 17/04; A61P 17/16
  See application file for complete search history.

(56) References Cited

U.S. PATENT DOCUMENTS

| | | | |
|---|---|---|---|
| 2013/0089583 A1* | 4/2013 | Taylor | A61K 8/26 8/405 |
| 2016/0374907 A1* | 12/2016 | Balian | A61K 8/895 424/401 |
| 2018/0116923 A1 | 5/2018 | Dudley et al. | |
| 2019/0105261 A1 | 4/2019 | Waugh et al. | |
| 2019/0216952 A1 | 7/2019 | Dinardo | |

\* cited by examiner

*Primary Examiner* — Robert A Wax
*Assistant Examiner* — Quanglong N Truong
(74) *Attorney, Agent, or Firm* — Nemphos Braue LLC; Michael Antone

(57) ABSTRACT

A sunscreen composition, containing an effective amount of Methylene Blue and/or a hydrate and or a pharmaceutically-acceptable salt thereof; an effective amount of one or more UVA and/or UVB absorbing compounds, with the proviso that Oxybenzone and Octinoxate are excluded; and an excipient base.

11 Claims, 6 Drawing Sheets

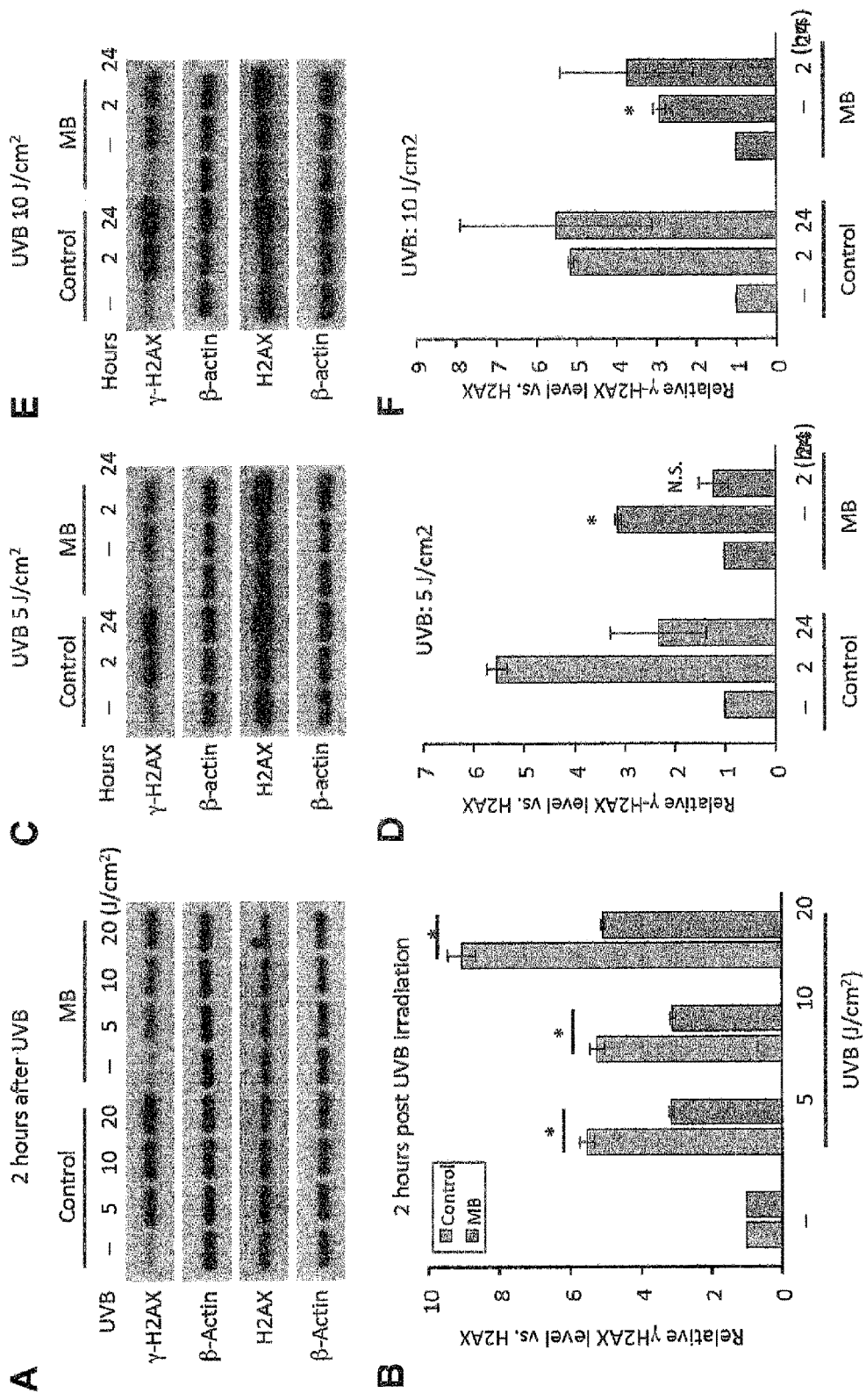
Figure 5  MB alleviates DNA damage induced by UVB irradiation in human keratinocytes
(* $p<0.05$ MB vs Control at the same dose or same time point)

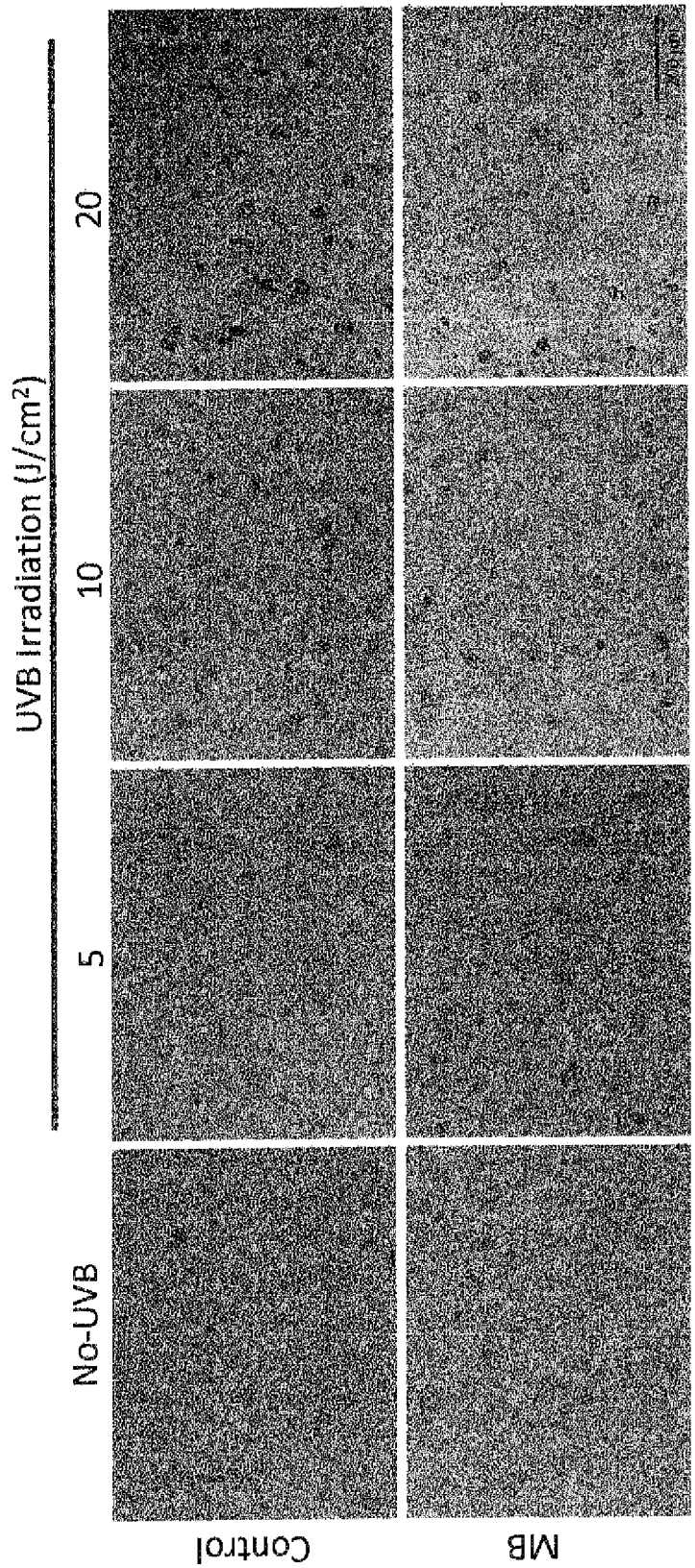
Figure 6 MB prevents human keratinocytes from UVB-induced cell death

INGREDIENT IN SUNSCREEN COMPOSITIONS

This invention was made with government support under No. 1842745 awarded by the National Science Foundation. The government has certain rights in the invention.

FIELD OF THE INVENTION

The present invention relates to novel active ingredient sunscreen compositions, which afford protection against both ultraviolet A (UVA) and ultraviolet B (UVB) solar radiation for human skin as well as reducing reactive oxygen species (ROS) and skin damage resulting from exposure to solar radiation.

DESCRIPTION OF THE BACKGROUND

Intrinsic aging of the skin occurs normally with aging. Extrinsic aging, however, is caused by damage to the skin by external agents. For example, damage to the dermal connective tissue of the skin is caused by exposure to UV-induced reactive oxygen species (ROS). Although ROS are produced within human cells as a natural by-product of metabolic reactions, UVA radiation from the sun significantly increases ROS levels beyond normal metabolic levels resulting in damage to skin cells and surrounding connective tissue. This damage leads to physical signs of extrinsic/premature photoaging, such as wrinkles and reduction in skin elasticity. Further, endogenous anti-oxidants are depleted with elevated levels of UVA-generated ROS, which is why many anti-aging skin care creams include exogenous antioxidants to help neutralize ROS and reduce their effects.

Sunscreen protects skin against sun damage from ultraviolet radiation, which contains UVA and UVB waves. UVB damages through burns and cancer-causing DNA mutations while UVA leads to photoaging as described above. Due to the singular Sun Protection Factor (SPF) standard, most sunscreens are more effective at blocking UVB radiation at the expense of often inadequate protection against UVA-induced photoaging.

Most current sunscreen products include Oxybenzone (2-hydroxy-4-methoxyphenyl)-phenylmethanone and/or Octinoxate (2-ethylhexyl p-cinnamate) as active UVB absorbers, however, these conventional sunscreen agents are now recognized as not only ineffective in blocking more damaging UVA radiation, but damaging in other respects. Oxybenzone has been assigned an EWG (environmental working group) hazard score of 8, on a scale of 1-10 (with 10 being the worst). The EWG score reflects both known and suspected hazards of ingredients on the human body.

In particular, recent evidence suggests that both Oxybenzone and Octinoxate are endocrine disrupters. Moreover, both Oxybenzone and Octinoxate have been demonstrated to hasten coral bleaching, and cause coral death. Consequently, at present, Hawaii, Palau, Bonaire and Key West, Florida have banned sunscreen formulations containing Oxybenzone and/or Octinoxate.

The American Academy of Dermatology Association (AADA) has reported that unprotected exposure to the sun's ultraviolet rays is a major risk factor for skin cancer. In fact, in February, 2019, the AADA announced that skin cancer is the most common cancer in the United States. Hence, a need exists for a solar-protective formulation that protects against both UVA and more damaging UVB solar radiation while avoiding all of the drawbacks attending the use of Oxybenzone and Octinoxate.

SUMMARY OF THE INVENTION

Accordingly, it is an object of the present invention to provide a sunscreen formulation which does not contain either Oxybenzone or Octinoxate.

It is also an object of the present invention to provide a sunscreen formulation which provides sufficient UVB as well as UVA protection of human skin.

It is also an object of the present invention to provide a sunscreen formulation which does not hasten coral bleaching, and does not harm corals.

Accordingly, the present invention provides a sunscreen formulation that contains Methylene Blue as an active ingredient in the formulation.

The present invention also provides a method of protecting human skin against the damaging effects of UVA and UVB solar radiation.

Furthermore, the present invention provides a method of effecting sunscreen protection that does not impose an unfavorable effect on coral health.

BRIEF DESCRIPTION OF THE DRAWINGS

FIG. 5 illustrates the protection afforded by MB-treated skin cells against DNA double-strand breakage versus a control group as evidenced by reduced levels of gamma-H2AX, which indicates reduced double-strand breakage.

FIG. 6 illustrates that MB provides the ability to partially rescue cell death after after subjecting MB-treated human keratinocyte cells to harsh UVB irradiation for 5 days versus control human keratinocyte cells.

DETAILED DESCRIPTION OF THE ILLUSTRATIVE EMBODIMENTS

Term Definitions

Figure 1:
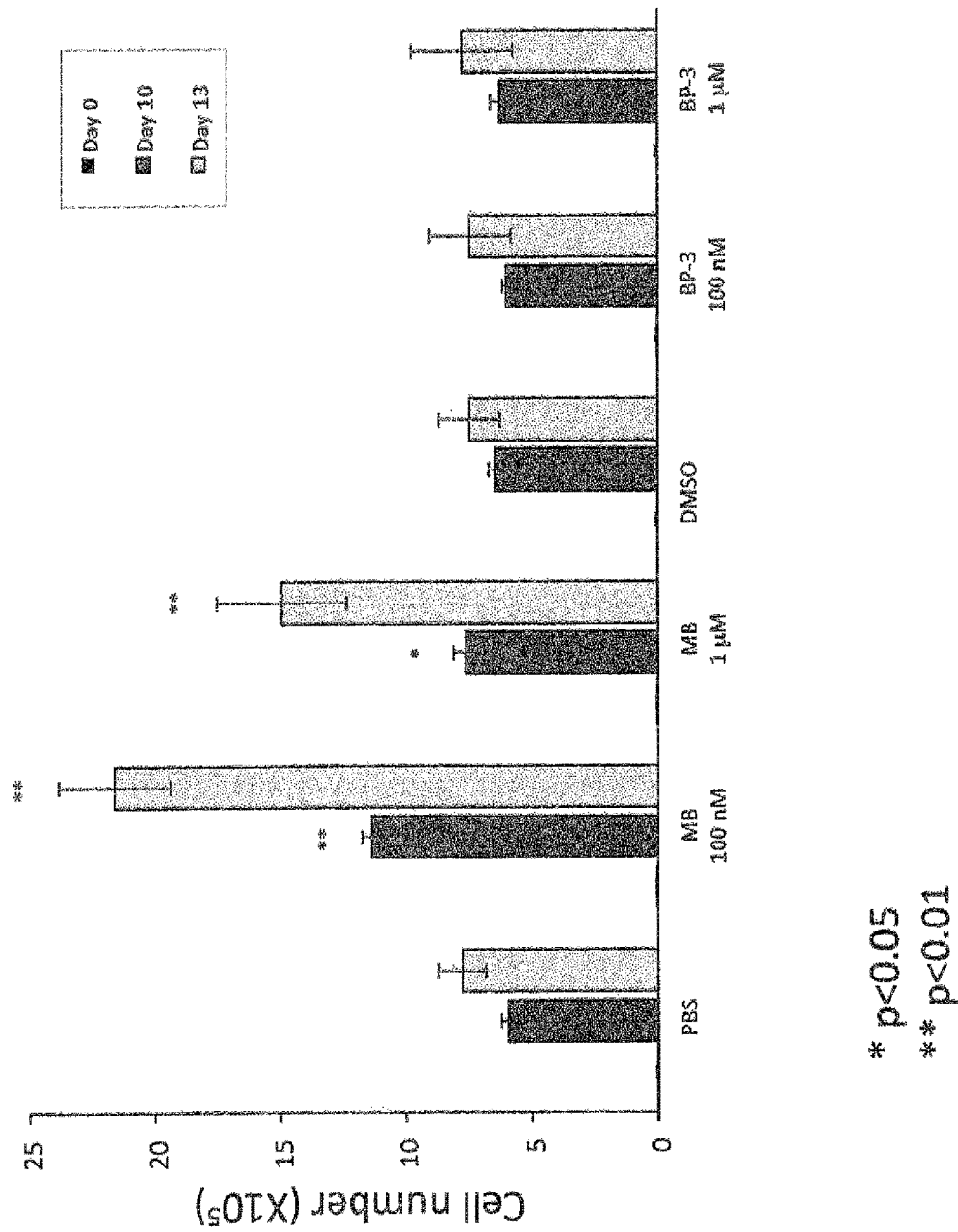
FIG. 1 illustrates the advantage of cell proliferation caused by Methylene Blue (MB) as compared to Oxybenzone (BP-3) and solvent controls PBS or 0.1% DMSO.

UVA radiation: 320-400 nm
UVB radiation: 280-320 nm
UVC radiation: 200-280 nm
Oxybenzone: 2-hydroxy-4-methoxyphenyl)-phenylmethanone,
Octinoxate: 2-ethylhexyl p-methoxycinnamate
Methylene Blue: [7-(dimethylamino) phenthiazin-3-yll-dene]-dImethylazinium chloride, or more simply as methylthloninium chloride. Also included are all hydrates, particularly, the hydrate or trihydrate of Methylene Blue as well as all dermatologically acceptable salts thereof, such as the chloride salt. All forms of Methylene Blue are also abbreviated herein as MB and are to be understood as such.
about: as used herein means±10%. Hence, for example, "about 10%" means from 9 to 11%.

compositional constituent %: unless Indicated, all such percentages given in this application are in wt. % based on the total weight of the composition.

conventional sunscreen excipients: means the conventional components of current sunscreen compositions, except for the active ingredients which are included to absorb UVA and UVB solar radiation. Examples of conventional sunscreen excipients or adjuvants, include, for example, xanthan gums, corn starch, film-forming polymers and/or copolymers, glycerin, emulsifiers, moisturizing agents and cosmetic ingredients. Further examples of conventional sunscreen composition excipients or adjuvants are described in U.S. Pat. Nos. 9,149,664; 8,128,913; 9,050,475 and 6,800,274, all of which are incorporated herein by reference in the entirety. The present invention specifically avoids the inclusion of Oxybenzone and/or Octinoxate in the aforementioned U.S. patents which are used as UVA and/or UVB absorbers, and uses instead, Methylene Blue or any of the hydrates or dermatologically-acceptable salts thereof. Further, it is explicitly contemplated that conventional inorganic compounds, such as zinc oxide and/or titanium oxide, for example, may be used in formulating the sunscreen composition of the present invention. Also, polymers and/or copolymers that are conventionally used as sunscreen stabilizer emollients, such as polyester-8, may also be used in the present sunscreen formulations.

Dermatologically-acceptable salts of MB: includes all salts recognized as safe for application to human skin, but generally, the chloride and/or hydrochloride salts are preferred.

In vitro 2D skin test: This test is described in by Xiong, et al. in *Scientific Reports* 7, Article number: 2475 (2017), using primary human skin cells (skin fibroblast cells or primary keratinocytes).

Sunscreen agents excluded from the present invention: the conventional sunscreen compounds Oxybenzone and Octinoxate are explicitly excluded from this invention. However, other conventional FDA-approved UVA and UVB absorbers may be used in combination with MB, its hydrates or salts in the present invention.

SPF: means a "sun protection factor" defined at 21 USC 352.1 et seq. using the term MED, which in turn means Minimal Erythema Dose, which is defined as the quantity of erythema-effective energy (expressed in Joules per square meter) required to produce the first perceptible redness reaction with clearly defined borders. Using MED, SPF is defined as the UV energy required to produce an MED on protected skin divided by the UV energy required to produce an MED on unprotected skin. i.e., SPF value=MED (protected skin (PS))/MED (unprotected skin (US)), where PS is the minimal erythema dose for protected skin after application of 2 milligrams per square centimeter of the final formulation of the sunscreen product. MED (US) is the minimal erythema dose for unprotected skin, i.e., skin to which no sunscreen has been applied.

Minimal Sunscreen Protection Product: defined in 21 USC 352.3 as providing an SPF value of 2 to under 12.

Moderate Sun Protection Product: defined in 21 USC 352.3 as providing an SPF value of 12 to under 30.

High Sun Protection Product: defined in 21USC 352.3 as providing an SPF value of 30 or above.

Essentially, if one burns after 20 minutes in the sun, an SPF 30 sunscreen product will provide protection for about 30×20 or 600 minutes, or about 10 hours. Also, it is noted that SPF 15 blocks 93% of UVB rays, and SPF 30 blocks 97% of UVB rays. SPF 50 and 100 block 98% and 99% of UVB rays, respectively.

FDA-Approved Sunscreen Active Ingredients:
  Aminobenzoic acid
  Avobenzone
  Cinoxate
  Dioxybenzone
  Homosalate
  Menthyl anthranilate
  Octocrylene
  Octyl Methoxycinnamate
  Octyl Salicylate
  Oxybenzone
  Padimate 0
  Phenylbenzimidazole Sulfonic Add
  Sulisobenzone
  Trolamine Salicylate
  Zinc Oxide
  Titanium Oxide Effective Amount of Active Sunscreen ingredient: as used herein means an amount of an active sunscreen ingredient effective as a filter against either UVA and/or UVB solar radiation in a concentration in a sunscreen composition not exceeding the FDA-approved upper concentration limit for any particular active sunscreen ingredient. A separate definition for MB effective amount is provided below.

Effective Amount of Methylene Blue (MB): means a concentration of MB and/or one or more of its hydrates and/or pharmaceutically-acceptable salts of from about 0.1 µM to about 2 µM based on the total sunscreen composition. Any concentration amount in this range may be used, however, it is preferred to use from about 0.2 µM to about 1.5 µM. These ranges explicitly refer to MB or any single hydrate or pharmaceutically-acceptable salt or combination thereof.

Pharmaceutically-acceptable: is used herein in the conventional usage, and also necessarily includes topically-acceptable.

FDA-approved sunscreen active ingredients known to block UVA radiation are avobenzone; benzophenones, such as Oxybenzone and dioxybenzone; mexoryl SX (Ecamsule) menthyl anthranilate, titanium dioxide and zinc oxide, for example. Some of these active ingredients absorb both UVA and UVB rays, such as Oxybenzone, for example, The International Commission on Illumination (CIE) has reported that the natural sunlight that reaches earth contains about 6% of ultraviolet (UV, 290-400 nm), about 55% of visible (VIS, 400-800 nm) and about 40% of Infrared (IR, 800-2450 nm) radiation. UV radiation is divided into three categories: UVC (200-280 nm), UVB (280-320) and UVA (320-400 nm). UVC does not reach the earth's surface as it is completely absorbed by the atmosphere, and much UVB is absorbed by oxygen and ozone. Hence, UVA constitutes about 95% of the UV radiation reaching the earth's surface. Yet, a single digit percentage of UVB radiation does reach the earth's surface. In comparison to UVA, shorter-wavelength UBV radiation can cause longer-term, more severe damage to the skin, including sunburns, DNA mutations and skin cancer.

Although the Food and Drug Administration (FDA) considers that most of the harmful effects from the sun are caused by UV radiation in the range of 280-370 nm, researchers outside of the FDA consider that skin photodamage can be caused by full spectrum solar radiation in the range of 290-800 nm and involves free radical mechanisms. Moreover, there is experimental evidence that conventional sunscreen filters, such as Oxybenzone and Octinoxate can enhance UV-induced reactive oxygen species (ROS) generation as determined by by fluorescence in epidermal skin models, The present invention is based, in part, on the unexpected discovery that Methylene Blue (MB) can be used as an effective UVB filter compound in lieu of conventional sunscreen filter compounds, such as, in particular Oxybenzone, and Octinoxate, for example, More specifically, it has been discovered that MB absorbs both UVA and UVS radiation and can, thus, be used to advantage as a sunscreen filter compound.

However, the present invention is also based in part upon the discovery that Mg boosts skin cell proliferation, and also reduces ROS levels in skin cells as compared to both oxybenzone and controls, Furthermore, the present invention is also based in part upon the discovery that MB effectively absorbs UVB radiation, but also promotes recovery of human skin cells after being subjected to UVB radiation as measured by cell viability and reduced double-strand DNA breakage.

Additionally, the present invention is based, in part, upon the unexpected discovery that MB poses no threat to the health of coral whereas both Oxybenzone and Octinoxate effect both coral bleaching and death in water samples containing either Oxybenzone or Octinoxate. Experiments by the Inventor have confirmed this result.

MB-Based Sunscreen Formulations

The present formulations generally contain an active sunscreen component, and an excipient component. The formulations of the present invention may be in the form of a cream, lotion, spray or stick.

Generally, as one principal active ingredient, MB and/or any of its hydrates and/or pharmaceutically-acceptable salts, is used in/are used in a concentration of from about 0.1 μM to about 2 μM based on the total sunscreen composition. More preferably, the concentration of MB and/or any of its hydrates and/or any of its pharmaceutically-acceptable salts used is from about 0.2 μM to about 1.5 μM. The principal active Ingredient MB may be supplemented by one or more USFDA-approved conventional organic sunscreen agents other than Oxybenzone and/or Octinoxate for use in the U.S., and one or more European Union-approved conventional organic sunscreen agents other than Oxybenzone and/or Octinoxate for use in Europe. If one or more such supplemental conventional organic sunscreen agents are Included in a formulation, the total amount of MB and/or any of its hydrates and/or any pf Its pharmaceutically-acceptable salts are used in the concentration range of from about 0.1 μM to about 2 μM based on the total sunscreen composition. More preferably, the concentration of MB and/or any of its hydrates and/or any of its pharmaceutically-acceptable salts is from about 0.2 μM to about 1.5 μM.

Examples of USFDA-approved organic conventional sunscreen (UVB absorbing) agents that may be used include, for example, aminobenzoic acid, cinoxate, homosalate, octocrylene, octisalate, octyl dimethyl 4-aminobenzoic acid, phenylbenzimidazole sulfonic acid, and triethanolamine salicylate. Examples of organic conventional sunscreen (UVA absorbers) agents that may be used include, for example, avobenzone, dioxybenzone, and sullsobenzone.

Also, the following European Union-approved conventional sunscreen agents may be used in conjunction with MB in Europe, for example: amiloxate (UVB absorber), bernotrizoline (UVA and UVB absorber), bisdisulizole (UVA and UVB absorber), bisoctrizole (UVA and UVB absorber), diethylamino hydroxybenzoyl hexyl benzoate (UVA absorber), ecamsule (UVB absorber), isotrizinol (UVB absorber), octyl triazone (UVB absorber), polysilicone-15 (UVB absorber), and tris-biphenyl triazine (UVB absorber). The above-listed supplemental organic conventional sunscreen agents are only exemplary and not an exhaustive list. However, any supplemental organic sunscreen agents must, of course, be approved for use by the appropriate governmental agency in the country of interest.

Generally, when additional convention organic sunscreen Ingredients are Included with MB in a formulation, the conventional organic sunscreen ingredients are Included in their normal amounts as in conventional sunscreen formulations. For example, 21 USC 352.10 specifies that any of the following active organic ingredients may be used within the concentrations specified for each ingredient (based upon the total weight of the sunscreen composition):

Aminobenzoic acid (PABA): up to 15% by wt.
Avobenzone: up to 3% by wt.
Cinoxate: up to 3% by wt.
Dioxybenzone: up to 3% by wt.
Homosalate: up to 15% by wt.
Menthyl anthranilate: up to 5% by wt.
Octocrylene: up to 10% by wt.
Octyl methoxycinnamate: up to 7.5% by wt.
Padimate 0: up to 6% by wt.
Phenylbenzimidazole sulfonic acid: up to 4% by wt.
Sulisobenzone: up to 10% by wt.
Trolamine salicylate: up to 12% by wt.

Aside from conventional organic supplemental sunscreen agents, the present sunscreen composition may also include Inorganic mineral sunscreen agents, such as zinc oxide and/or titanium dioxide. These inorganic compounds are generally coated with inert substances, such as silica, alumina, stearic acid or silicone compounds, for example, when used in sunscreen formulations. Otherwise, uncoated titanium dioxide emits excited electrons after UV absorption which can generate free radicals. Uncoated zinc oxide can modify the pH of the sunscreen formulation and form zinc hydroxide, releasing hydroxide ions into the formulation. The particle coating also prevents agglomeration of inorganic particles and keeps the pigments dispersed in the formulation. Coating of such inorganic particles is well-known in the art. See, for example, U.S. Pat. No. 5,756,788, which is incorporated herein in the entirety.

Further, when included in sunscreen formulations, coated zinc oxide and titanium dioxide particles are used as nanopartides as this enhances skin protection by enabling greater formulation homogeneity. Particles of a size of about 35 nm are large enough to absorb, scatter and reflect short-wavelength UV radiation, while remaining invisible to longer-wavelength visible light. The optimum particle size for these coated inorganic particles has been reported to be between about 40 and 60 nm. Production of such nanoparticles are their coatings are both well-known in the art.

21 USC 352.10 specifies that each of zinc oxide and titanium oxide may be present in an amount of up to 15% by wt, based on the total weight of a sunscreen formulation.

Both avobenzone and zinc oxide are used specifically as UVA filters, and homosalate, octisalate, octocrylene and titanium dioxide are used specifically as UVB filters in the U.S., for example.

The excipient component may be a single- or multiple-component excipient. Examples of conventional sunscreen composition excipients may be those from the above-noted incorporated U.S. patents, as well as from U.S. Pat. No. 6,409,997 (wax cosmetic stick) and U.S. Pat. No. 8,420,062 (a spray formulation), the latter two of which are also Incorporated herein in the entirety by reference. As noted above, the present invention may be used with any conventional sunscreen composition and form of composition, i.e., cream, lotion, spray or stick, provided that MB, or any of its hydrates or salts, are used as the active ingredient or Ingredients that absorb UVA and UVB solar radiation in addition to one or more conventional organic sunscreen agents as noted above with the exception of Oxybenzone and Octinoxate.

Further, it is explicitly contemplated that MB may be used in the present Invention as a single compound or as a mixture of the single compound with one or more hydrates and/or salts of MB. For example, the active ingredient in the sunscreen composition of the present invention may be MB+MB trihydrate and MB chloride, with the total concentration being from about 0.1 µM to about 2 µM, and preferably from about 0.2 µM to about 1.5 µM as noted above.

Preferably, the concentration of MB or any of its hydrates or pharmaceutically-acceptable salts in the present sunscreen compositions is from about 0.2 µM to about 1.5 µM, and even more preferably from about 0.4 µM to about 1.0 µM. For example, an exemplary total concentration range is about 0.4, 0.5, 0.6. 0.7 or 0.8 µM for MB and/or any of its hydrates and/or any of its pharmaceutically-acceptable salts. However, any concentration in the range of 0.1 to 2 µM may be used.

Further, any of the excipients from U.S. Pat. No. 9,050,475, defined as other than conventional organic compound-UVA and/or UVB absorbers, may be used in the present sunscreen compositions. U.S. Pat. No. 9,050,475 is incorporated herein in the entirety by reference.

Illustrative examples of excipients that may be used with the present sunscreen compositions include, for example:
A) Inorganic sunscreen agents, such as zinc oxide and/or titanium oxide;
B) Moisturizing agents, emollients, vitamins, botanical extracts, fragrances, coloring ingredients, thickening agents and emulsifiers; and
C) Essential oils obtained from herbs, flowers and other plants.

Designing Sunscreen Formulations

A facile manner of developing a suitable sunscreen formulation is to refer to the BASF Sunscreen Simulator, publicly available at www.basf.com/sunscreen-simulator. The BASF simulator first informs the user of approved UV filters for any region chosen. Second, the BASF simulator takes into account the photo-stability of each UV absorber and of certain UV filter combinations that are known to either stabilize or destabilize each other. Third, the simulator also shows how closely a given UV filter combination reaches the profile of the ideal sunscreen, which is a flat profile throughout the relevant UVB and UVA range from about 280 to 400 nm. See https://www.sunscreensimulator.basf.com.

The present sunscreen composition may be contained in a bottle, metal tube, laminate tube, plastic tube, dispenser, pressurized container, package, or lipstick container, for example. The composition may be dispensed as a spray, foam, aerosol, liquid, fluid or semi-solid.

The present invention will now be illustrated by certain examples which are provided solely for purposes of illustration, and which are not intended to be limitative.

Example 1

Using an in vitro 2D skin model, MB was tested against oxybenzone (BP-3), the latter being the most popular UVA/UVB filter in the U.S., at concentrations of 100 nM and 1 µM for each. A solvent of 0.01% phosphate-buffered saline (PBS) was applied as a control. After 13 days, results were observed.

The MB-treated samples at both concentrations exhibited an increase in cell proliferation. Specifically, from FIG. 1, the greatest cell number reading was obtained for MB at a concentration of 100 nM, with the MB sample at a concentration of 1 µM being somewhat less. In contrast, no changes in growth were observed in the BP-3 treated cells relative to control treatment, suggesting that at concentrations of 100 nM and 1 M, BP-3 is at least relatively safe.

Example 2

Figure 2:
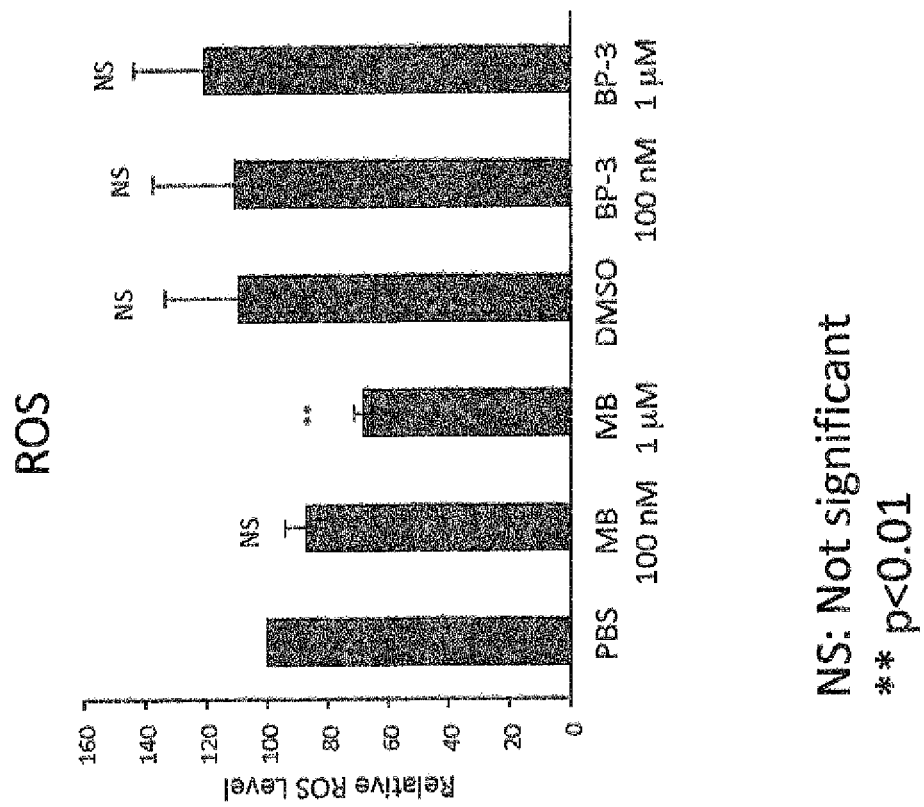
FIG. 2 illustrates the superior ability of MB as a UVA-induced ROS scavenger as compared to both controls and Oxybenzone (BP-3).

Using the same in vitro 2D skin model as in Example 1, MB was again tested against oxybenzone (BP-3) using the same two concentrations as in Example 1 and using 0.1% dimethyl sulfoxide (DMSO) as a solvent control. Cellular reactive oxygen species (ROS) levels, as determined by MitoSOX, were quantified. In the ROS analysis, elevated ROS levels were noted in the BP-3 treated cells, in contrast to dosage-dependent reduction in ROS in MB-treated cells. See FIG. 2. The results of both Example 1 and 2 indicate that MB is a much more effective UVA scavenger than BP-3 when used at the same concentration. See FIG. 2.

Example 3

UVB radiation can cause longer-term, more severe damage to the skin than UVA radiation. UVB radiation can not only cause sunburns, but also DNA mutations and skin-cancer.

Figure 3:
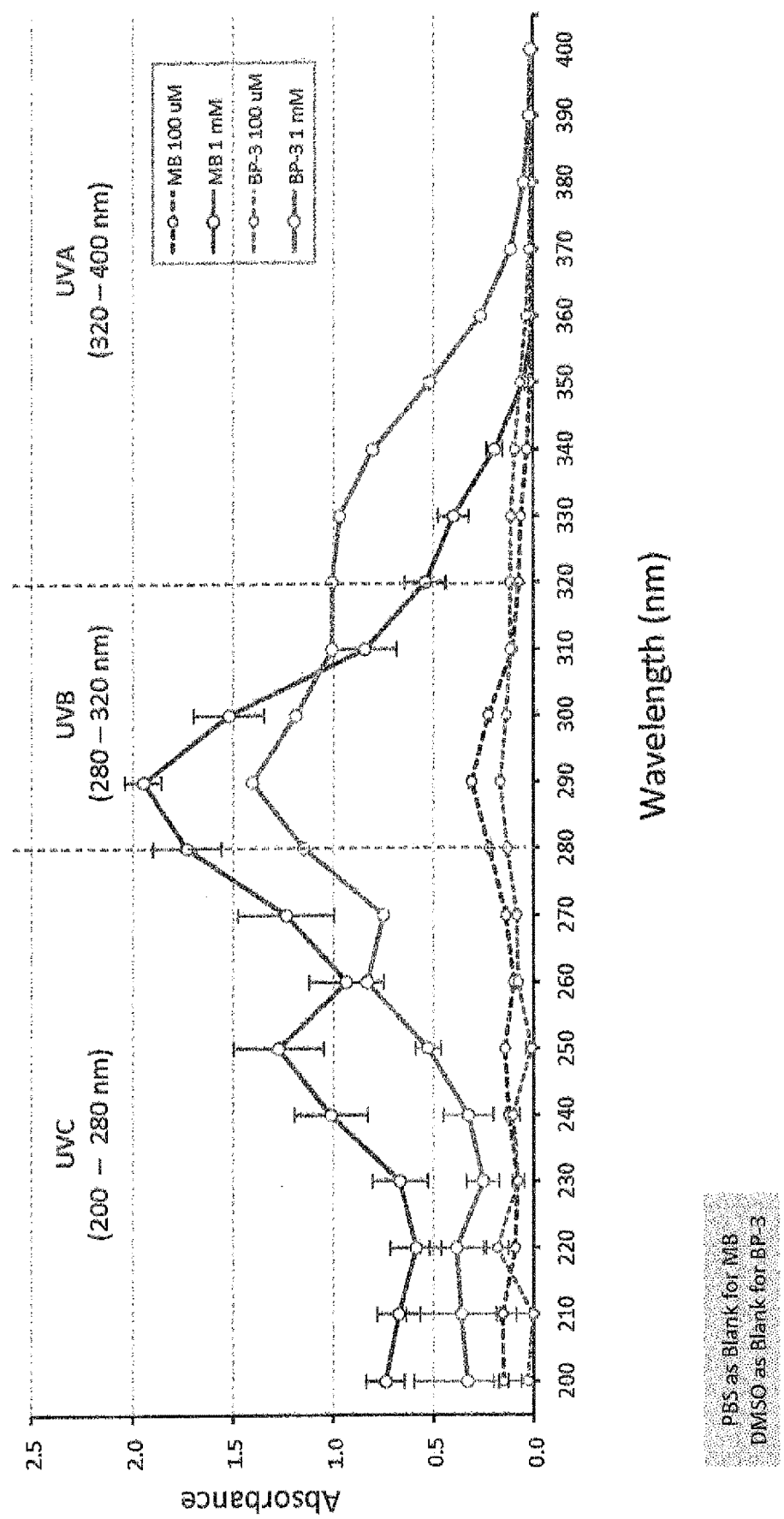
FIG. 3 illustrates the superior ability of MB as a UVB absorber as compared to Oxybenzone (PB-3), and PBS as a blank (control) for MB and DMSO as a blank (control) for PB-3.

In this example, the absorption characteristics based on spectrophotometric analysis of various dilute solutions of each of MB and oxybenzone (BP-3) were measured and then compared. The solution concentrations for each of MB and BP-3 were 100 µM and 1 mM. The results obtained are shown in FIG. 3. Note the surprising superior protection against UVB radiation provided by MB versus BP-3 with both at a concentration of 1 mM.

Example 4

In this example, the protection ability of MB against UVB radiation was measured. The present inventor previously demonstrated that MB can stimulate the DNA repair process by upregulating DNA damage repair pathway factors, such as PARPI, which can possibly undo DNA damage from UVB radiation. Here, a preliminary study was conducted in which human skin fibroblasts were pre-treated with MB at 100 nM concentration for two weeks and then exposed to 0, 5, 10 and 20 seconds of UVB radiation at 1100 mW/cm$^2$.

Figure 4:
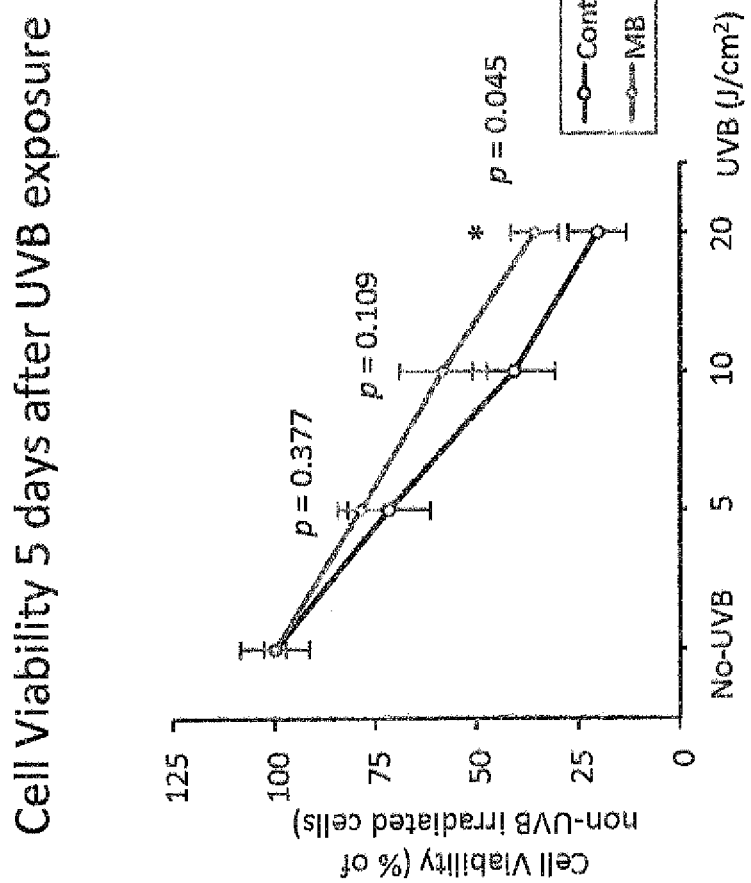
FIG. 4 illustrates the superior ability of MB-exposed skin cells versus untreated skin cells to recover from high-dose exposure to UVB radiation as measured by cell viability at 5 days post-treatment.

In this preliminary study, both groups, i.e., MB-exposed skin cells and the control group, were exposed to the same amount of UVB radiation. After five (5) days recovery, observation showed that the MB-treated group exhibited a significantly superior recovery versus the control group. See FIG. 4.

This was further confirmed by imaging analysis that showed a superior survival of MB-treated samples versus control samples after exposure to high dosage-UVB radiation. Specifically, the histone H2AX Is phosphorylated to a gamma form (gamma H2AX) upon DNA double strand breakage and levels of gamma H2AX positively correlate with the presence of DNA breaks, which are commonly generated by UVB radiation. Moreover, at 24 hours after UVB exposure, the skin cells that were exposed to MB had reduced levels of gamma H2AX, while the control group doubled the cellular levels of gamma H2AX. Hence, this example demonstrates that MB can play a significant role in reversing DNA damage from UVB radiation. See FIGS. 5 and 6.

As noted above, the present invention explicitly contemplates all physical forms of sunscreen compositions containing MB or any of its hydrates or dermatologically-acceptable salts. Several examples of these diverse compositions are provided below. These examples are solely provided for purposes of Illustration and are not intended to be limitative.

Example 5

A sunscreen excipient base is prepared as follows:
43% by wt. of water,
5 wt. % of poly(maleic acid/methylvinylether) compolymer
46 wt. % of poly(vinylpyrrolidone/hexadecene) polymer
5.5 wt. % of poly(vinylpyrrolidone/eicosene) polymer
0.5 wt. % of preservative
The polymeric excipient base is prepared as Indicated in Example 1 of U.S. Pat. No. 8,128,913.
To this base is added an amount of avobenzone sufficient to reach a final concentration of 2% by wt. based on the total weight of the composition.
To this is added an amount of MB sufficient to raise the final concentration of 0.5 µM of MB based on the total composition.

Example 6

A sunscreen composition is prepared as a stick formulation in accordance with Example 1 of U.S. Pat. No. 9,050,475, and Table 2 thereof, except that octocrylene, octisalate and meridimate of this patent is replaced with Methylene Blue in an amount of 2 wt. % based on the total weight of the stick formulation.

Example 7

A sunscreen composition is prepared as a spray formulation in accordance with Example 2 and Table 4 of U.S. Pat. No. 9,050,475, except that sunscreen nos. 5, 6, 7 and 8 are replaced by MB in an amount sufficient to reach a concentration of MB of 1 µM based on the total composition, and an effective amount of avobenzone.

Additional formulations for the present sunscreen compositions may be based upon U.S. Pat. No. 6,464,965 and US 2013/0266527, both of which are incorporated herein in their entirety. For both, the present Invention uses MB, its hydrates or salts as a necessary component or components of the UVA and UVB absorbers in the sunscreen composition.

Example 8

An oil-in-water (O/W) emulsion including an aqueous phase and an oil phase is prepared with MB solubilized in the aqueous phase, and zinc oxide dispersed in the oil phase. An amount of MB is added to the aqueous phase sufficient to reach a concentration of 0.5 µM in the final total composition, and an effective amount of zinc oxide is added to the oil phase.
To the aqueous phase is added an effective amount of a crosslinked carboxylic acid polymer, and a buffering system and at least one stabilizing agent, such as surfactants, emulsifiers, chelating agent or combinations thereof, and maintaining the pH of the aqueous phase in the range of 7.5 to 8.8. See U.S. Pat. No. 6,464,965.

Example 9

A high SPF sunscreen composition may be prepared containing an effective amount of MB; an effective amount of an oil-soluble UVA absorber; a non-ionic surfactant, such as polyoxyethylene sorbitan alkyl esters with saturated C12 to C16 carbon chain and having an HLB greater than 12, or polyoxyethylene sorbitan alkyl esters with unsaturated c18 carbon chain and having an HLB greater than 9; and an excipient. See US 2013/0266527.

Example 10

Samples of *Umbrella xenia* were placed in individual containers filled with seawater plus any one of MB or Oxybenzone or Octinoxate for one week. All of the containers were otherwise under the exact same temperature, lighting and water flow conditions. Separate containers were used for both "Control" (nothing added) and DMSO, also added in the same two concentrations specified below for MB, Oxybenzone and Octinoxate.

No adverse effects were observed on the soft corals when MB was used in the seawater. However, harmful effects for each of Oxybenzone and Octinoxate were observed on coral reef growth and regeneration. At the tested concentrations of 0.5 and 1.0 µM for all of the MB, Oxybenzone and Octinoxate samples, both the Oxybenzone and Octinoxate samples resulted in coral bleaching and subsequent coral death in less than one week.

The use of the disclosed sunscreen composition prior to entering any ocean water which may contain coral growth, particularly in close proximity, will avoid the adverse effects on coral health observed from Oxybenzone and Octinoxate, including coral death.

The use of micromolar concentrations described herein for MB and/or any hydrates and/or any pharmaceutically-acceptable salts thereof refers to the number of micromoles per 1 liter volume of total sunscreen composition. Methylene Blue, for example, has a molecular weight of 319.85 grams per mole. The desired content of MB and/or any hydrate and/or any pharmaceutically-acceptable salt may be conveniently determined on that basis by one of ordinary skill in the art.

As noted above, the examples provided are Illustrative and are not Intended to be limitative.

What is claimed is:
1. A sunscreen composition, comprising:
   a) an effective amount of Methylene Blue and/or a hydrate and/or a pharmaceutically-acceptable salt thereof in a concentration of about 0.1 µM to about 2 µM based on the total sunscreen composition to serve as at least a UVB filtering compound;
   b) an effective amount of one or more UVA filtering and/or absorbing compounds, with the proviso that Oxybenzone and Octinoxate are excluded; and
   c) an excipient base.
2. The sunscreen composition of claim 1, wherein component b) comprises an inorganic mineral compound, comprising zinc oxide and/or titanium oxide.
3. The sunscreen composition of claim 1, which is in a form of a spray.
4. The sunscreen composition of claim 1, which is in a form of a stick.

5. The sunscreen composition of claim 1, which is in a form of a lotion or cream.

6. The sunscreen composition of claim 1, which is in a form of a lip balm.

7. The sunscreen composition of claim 1, wherein component a) is aqueous-based, and component b) is oil-based.

8. The sunscreen composition of claim 1, wherein the total concentration of Methylene Blue and/or any of its hydrates and/or any of its salts is from 0.4 to 0.8 µM based on the total sunscreen composition.

9. A method of protecting human skin from UVA and/or UVB solar radiation, which comprises applying the composition of claim 1, to an area of said human skin to be protected.

10. A method of preparing a sunscreen composition, which comprises admixing an effective amount of Methylene Blue and/or any hydrate and/or pharmaceutically-acceptable salt thereof with a topically-acceptable excipient in a concentration of 0.1 µM to about 2 µM of Methylene Blue based on the total sunscreen composition to serve as at least a UVB filtering compound.

11. The method of claim 10, which further comprises admixing one or more UVA and/or absorbing compounds, with the proviso that Oxybenzone and Octinoxate are excluded.

\* \* \* \* \*